United States Patent [19]

Wendler et al.

[11] 3,998,849
[45] Dec. 21, 1976

[54] 2α-(2-CARBOXY-2-FORMYLETHYL)-3β-HYDROXY-5-OXO-1β-CYCLOPENTANE-TANOIC ACID AND PROCESS

[75] Inventors: Norman L. Wendler, Summit; David Taub, Metuchen; Harry L. Slates, Westfield; Zbigniew S. Zelawski, Piscataway, all of N.J.

[73] Assignee: Merck & Co., Inc., Rahway, N.J.

[22] Filed: May 8, 1975

[21] Appl. No.: 575,676

Related U.S. Application Data

[62] Division of Ser. No. 435,812, Jan. 23, 1974, Pat. No. 3,915,994, which is a division of Ser. No. 201,979, Nov. 24, 1971, Pat. No. 3,833,612.

[52] U.S. Cl. .................... 260/340.9; 260/514 D
[51] Int. Cl.$^2$ ..................... C07D 317/72
[58] Field of Search ................. 260/340.9

[56] References Cited
UNITED STATES PATENTS

| | | | |
|---|---|---|---|
| 3,890,351 | 6/1975 | Taub | 260/340.9 |
| 3,899,525 | 8/1975 | Oda et al. | 260/340.9 X |

OTHER PUBLICATIONS

Taub et al., Chem. Communications, pp. 1258–1259 (1970).

*Primary Examiner*—Ethel G. Love
*Attorney, Agent, or Firm*—Thomas E. Arther; Harry E. Westlake, Jr.; Rudolph J. Anderson, Jr.

[57] ABSTRACT

Racemic or optically-active prostaglandin $E_1$ is synthesized from racemic or optically-active precursors in good yield at the various steps from 3α,6,7,7α-tetrahydro-4-methyl-2-oxo-1β-indaneheptanoic acid methyl ester proceeding through 2α-(2-carboxyethyl)-3β-hydroxy-5-oxo-1β-cyclopentaneheptanoic acid methyl ester, δ-lactone, 5-cyclic ethylene acetal, 2α-(2-carboxy-2-formylethyl)-3β-hydroxy-5-oxo-1β-cyclopentaneheptanoic acid methyl ester, δ-lactone, 5-cyclic ethylene acetal, 2α-(2-carboxy-2-oxoethyl)-3β-hydroxy-5-oxo-1β-cyclopentaneheptanoic acid methyl ester, δ-lactone, 5-cyclic ethylene acetal, and 3β-hydroxy-2α-(3-oxo-1-octenyl)-5-oxo-1β-cyclopentaneheptanoic acid methyl ester, 5-cyclic ethylene acetal.

3 Claims, No Drawings

2α-(2-CARBOXY-2-FORMYLETHYL)-3β-HYDROXY-5-OXO-1β-CYCLOPENTANEHEPTANOIC ACID AND PROCESS

This application is a division of U.S. Ser. No. 435,812, filed, Jan. 23, 1974, now U.S. Pat. No. 3,915,994, issued Oct. 28, 1975; which in turn is a division of U.S. Ser. No. 201,979, filed Nov. 24, 1971, now U.S. Pat. No. 3,833,612, issued Sept. 3, 1974.

BRIEF SUMMARY OF THE INVENTION

This invention relates to a new and novel synthesis of prostaglandin $E_1$, and more particularly to a synthesis which has a high degree of stereoselectivity at the points of generating the asymmetric centers of the molecule and produces either racemic or optically-active prostaglandin $E_1$, the activity corresponding to that of naturally-occurring prostaglandin $E_1$. It relates further to a synthesis in which the yields are high in the several reaction steps. The invention relates still further to the novel compounds obtained as intermediates in the (+) and (−) prostaglandin $E_1$ synthesis and to the process for making such intermediates.

DETAILED DESCRIPTION OF THE INVENTION

Prostaglandin $E_1$, which may be depicted structurally as

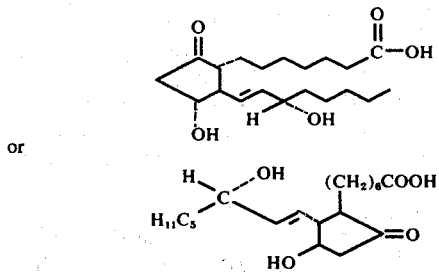

or is one of a group of naturally-occurring compounds known generally as prostaglandins. These prostaglandins have interesting and important biological activity, the precise biological properties varying with the individual members of the prostaglandin family, as described in the article Prostaglandins, by P. W. Ramwell et al., Progress in the Chemistry of Fats and Other Lipids, Vol. IX, Polyunsaturated Acids, Part 2, pp. 231-273, Pergamon Press (1968).

One of the more important prostaglandins is prostaglandin $E_1$, also known as $PGE_1$. It has an effect on the contractility of smooth muscle and is useful in the induction of labor in pregnant females and for the termination of pregnancies by therapeutic abortion, M. P. Embrey, British Medical Journal, 1970, 2, 256-258; 258-260. Other uses, besides stimulation of smooth muscle, are described in the literature and includes the lowering of blood pressure, effect on the mobilization of free fatty acids from adipose tissue, inhibition of lipolysis, and bronchodilating effects.

Heretofore, the supply of prostaglandin $E_1$, as well as of other prostaglandins, has been severely limited because only minute amounts of naturally-occurring material are available, and partial biosynthesis by enzymes present in mammalian seminal vesicles has only afforded limited amounts of the products.

An object of this invenion is to provide a stereoselective synthesis of (+) prostaglandin $E_1$, which compound has one-half the biological activity of the naturally-occurring $PGE_1$, and (−) prostaglandin $E_1$, which compound has 100% of the biological activity of naturally-occurring $PGE_1$, and which may be used for the same biological effects as the natural compound.

A further object of the invention is to provide novel intermediate compounds some of which, in addition to being useful in the synthesis of (+) and (−) $PGE_1$, may themselves exhibit prostaglandin-like activity. An additional object is to provide a stereoselective total synthesis of the other members of the prostaglandin group which may be prepared by known methods from (+) and (−) prostaglandin $E_1$. Thus, for instance, (+) prostaglandin $F_{1\alpha}$ may be obtained by reduction of (+) $PGE_1$. Other objects will become evident from the following description of the invention.

The novel process and intermediates of our invention are shown structurally in the following flow diagram; and, immediately following this diagram, the chemical names of the compounds are set forth.

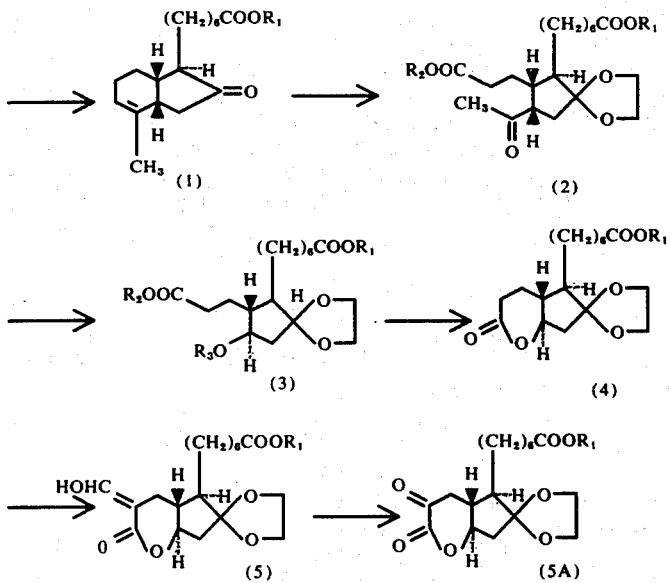

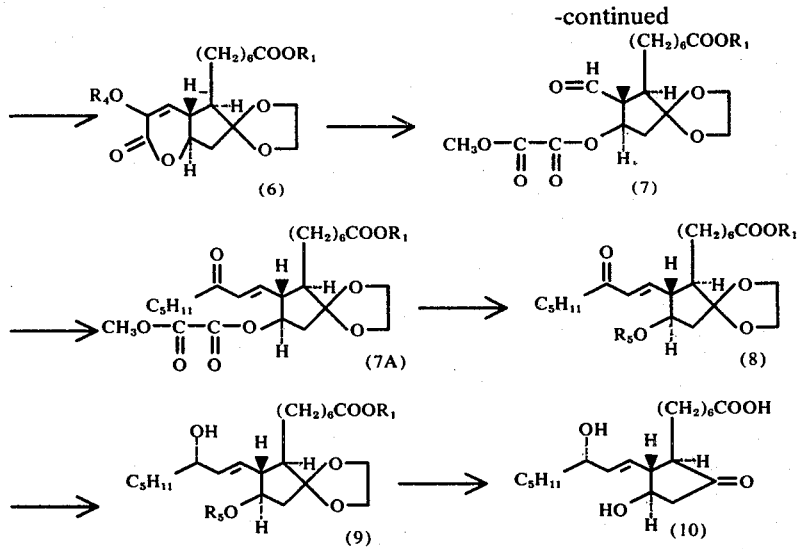

In the foregoing formulas $R_1$ and $R_2$ represent hydrogen, loweralkyl or aralkyl; $R_3$ represents hydrogen or an acetyl group, and $R_4$ and $R_5$ represent hydrogen or acyl. The loweralkyl groups of this invention are those containing from 1 to 6 carbon atoms such as methyl, ethyl, propyl, and hexyl. The acyl groups of this invention are loweralkanoyl groups of from 2 to 6 carbon atoms such as acetyl, propionyl, butyryl, hexanoyl, and the like, and monocyclic aroyl groups such as benzoyl, toluoyl, and the like. The aralkyl groups are defined as loweralkyl groups substituted with an aromatic group of from 6 to 10 carbon atoms. Preferred are benzyl, xylyl and the like.

As a matter of convenience for understanding the foregoing flowsheet and the following description of the invention, there follows a list of names of the chemical compounds 1-10 inclusive.

1. ($R_1$=$CH_3$) 3α,6,7,7α-tetrahydro-4-methyl-2-oxo-1β-indaneheptanoic acid methyl ester, 2-cyclic ethylene acetal.

2. ($R_1$=$CH_3$, $R_2$=H) 3-acetyl-2α-(2-carboxyethyl)-5-oxo-1β-cyclopentaneheptanoic acid methyl ester, 5-cyclic ethylene acetal.

2. ($R_1$=$R_2$=$CH_3$) 3β-acetyl-2α-[2-methoxycarbonyl)ethyl]-5-oxo-1β-cyclopentaneheptanoic acid methyl ester, 5-cyclic ethylene acetal.

3. ($R_1$=$R_2$=$CH_3$, $R_3$=acetyl) 3β-acetoxy-2α-[2-(methoxycarbonyl) ethyl]-5-oxo-1β-cyclopentaneheptanoic acid methyl ester, 5-cyclic ethylene acetal.

3. ($R_1$=$R_2$=$CH_3$, $R_3$=H) 2α-[2-methoxycarbonylethyl]-3β-hydroxy-5-oxo-1β-cyclopentaneheptanoic acid methyl ester, 5-cyclic ethylene acetal.

4. ($R_1$=$CH_3$) 2α-(2-carboxyethyl)-3β-hydroxy-5-oxo-cyclopentaneheptanoic acid methyl ester, -lactone, 5-cyclic ethylene acetal.

5. ($R_1$=$CH_3$) 2α-(2-carboxy-2-formylethyl)-3β-hydroxy-5-oxo-1β-cyclopentaneheptanoic acid methyl ester, -lactone, 5-cyclic ethylene acetal.

5A. 2α-(2-Carboxy-2-oxoethyl)-3β-hydroxy-5-oxo-1β-cyclopentaneheptanoic acid methyl ester, -lactone, 5-cyclic ethylene acetal.

6. ($R_1$=$CH_3$, $R_4$=acetyl) 2α-(2-acetoxy-2-carboxyvinyl)-3β-hydroxy-5-oxo-1β-cyclopentaneheptanoic acid methyl ester, -lactone, 5-cyclic ethylene acetal.

7. ($R_1$=$CH_3$) 2α-formyl-3β-[(methoxalyl)oxy]-5-oxo-1β-cyclopentaneheptanoic acid methyl ester, 5-cyclic ethylene acetal.

7A. ($R_1$=$CH_3$) 3β-[(methoxalyl)oxy]-2α-(3-oxo-1-octenyl)-5-oxo-1β-cyclopentaneheptanoic acid methyl ester, 5-cyclic ethylene acetal.

8. ($R_1$=$CH_3$, $R_5$=H) 3β-hydroxy-2α-(3-oxo-1-octenyl)-5-oxo-1β-cyclopentaneheptanoic acid methyl ester, 5-cyclic ethylene acetal.

9. ($R_1$=$CH_3$, $R_5$=H) Prostaglandin $E_1$ methyl ester, cyclic ethylene acetal.

9. ($R_1$=$R_5$=H) Prostaglandin $E_1$, cyclic ethylene acetal.

10. Prostaglandin $E_1$.

In the foregoing list of names and in subsequent discussions, the esters and acyl groups have been referred to as methyl esters and acetyl groups respectively because the detailed examples refer to such groups; but it is to be understood that other esters are within the scope of the invention as shown by the symbols $R_1$, $R_2$, $R_3$, and $R_4$ in the flow diagram.

The synthesis of prostaglandin $E_1$ in its racemic (+) or natural (−) form starts with 3α,6,7,7α-tetrahydro-4-methyl-2-oxo-1β-indaneheptanoic acid methyl ester (1, $R_1$=$CH_3$) in its racemic or optically active form.

In the first step of this synthesis either racemic or optically active 3α,6,7,7α-tetrahydro-4-methyl-2-oxo-1β-indaneheptanoic acid methyl ester (1, $R_1$=$CH_3$) is converted to 3α,6,7,7α-tetrahydro-4-methyl-2-oxo-1β-indaneheptanoic acid methyl ester, cyclic ethylene acetal by reaction with ethylene glycol in the presence of an acid such as p-toluene-sulfonic acid. The resulting acetal is then oxidized with an oxidizing agent such as potassium permanganate preferably in the presence of sodium periodate, to produce 3-acetyl-2α-(2-carboxyethyl)-5-oxo-1β-cyclopentaneheptanoic acid methyl ester, 5-cyclic ethylene acetal (2, $R_1$=$CH_3$, $R_2$=H). It is preferred to include potassium carbonate in the reaction system which facilitates the oxidation as well as partially epimerizing the 3-carbon atom such that the α-acetyl group becomes a β-acetyl group. The reaction product is a mixture of 3α-acetyl and 3β-acetyl-2α-(2-carboxyethyl)-5-oxo-1β-cyclopentaneheptanoic acid methyl ester, 5-cyclic ethylene acetal (2 $R_1$=$CH_3$, $R_2$=H).

The epimeric mixture is then treated with an excess of a diazoloweralkane or diazoaralkane to prepare the ester derivative which is then epimerized, forming the 3β-acetyl group from the 3α-acetyl group, with an alkali metal loweralkoxide, preferably the same alkoxide group present on the ester functions in order to prevent transesterification. In order to accomplish this the epimeric mixture is dissolved in a loweralkanol and treated with a loweralkanol solution of the alkali metal alkoxide at from 10° to 50° C., preferably room temperature, for from 10 to 30 hours, affording all 3β-acetyl-2α-[2-methoxycarbonylethyl]-5-oxo-1β-cyclopentaneheptanoic acid methyl ester, 5-cyclic ethylene acetal (2, $R_1=R_2=CH_3$), with no traces of the 3α-acetyl derivative.

Compound 2-($R_1=R_2=CH_3$) is then oxidized with an oxidizing agent as much as an organic peracid, preferably trifluoro peracetic acid, m-chloroperbenzoic acid and the like, affording 3β-acetoxy-2α-[2-methoxycarbonylethyl]-5-oxo-1β-cyclopentaneheptanoic acid methyl ester, 5-cyclic ethylene acetal (3, $R_1=R_2CH_3$, $R_3$=acetyl). The reaction mixture is generally buffered with a weakly alkaline buffering agent such as sodium monohydrogen phosphate. The reaction is run generally at room temperature for from 10 to 30 hours. Thin layer chromatography of an aliquot portion indicates the degree of completion of the reaction and additional oxidizing agent may be added if necessary until the reaction is complete.

Compound 3($R_1=R_2=CH_3$, $R_3$=acetyl) is treated with an alkali metal alkoxide in the corresponding loweralkanol. The reaction is run for from 1 to 4 hours at about room temperature and worked up by techniques known to those skilled in the art affording 2α-[2-methoxycarbonylethyl]-3β-hydroxy-5-oxo-1β-cyclopentaneheptanoic acid methyl ester, 5-cyclic ethylene acetal (3, $R_1=R_2=CH_3$, $R_3$=H). The hydroxy compound is then lactonized with an alkali metal alkoxide preferably potassium t-butoxide in an inert solvent such as benzene, toluene, and the like at the reflux temperature of the solvent employed. The solvent is preferably one which codistills with the loweralkanol corresponding to $R_2$.

Distillation of the solvent is continued until a thin layer chromatogram of an aliquot indicates conversion to lactone 4 is complete. This normally requires from 1 to 6 hours of distillation. There is recovered 2α-(2-carboxyethyl)-3β-hydroxy-5-oxo-1β-cyclopentaneheptanoic acid methyl ester, δ-lactone, 5-cyclic ethylene acetal (4, $R_1=CH_3$).

The next step in the racemic or optically active synthesis is the formylation of compound 4 with a loweralkyl formate in the presence of an alkali metal hydride at from 0° to 40° C. for from ½ to 6 hours. The exothermal nature of the reaction usually necessitates adding the alkali metal hydride portionwise and maintaining the temperature at from 0° to 10° during the first hour of the reaction. The product is 2α-(2-carboxy-2-formylethyl)-3β-hydroxy-5-oxo-1β-cyclopentaneheptanoic acid methyl ester, δ-lactone, 5-cyclic ethylene acetal soduim salt, which on treatment with a mild acid such as sodium dihydrogen phosphate in aqueous solution liberates compound 5-($R_1 = CH_3$).

The formyl derivative is ozonized in the presence of an organic base such as pyridine at temperatures substantially below 0° C., preferably dry ice temperatures, by bubbling ozone or a mixture of $O_2$ and $O_3$ into the reaction mixture until an excess is present, indicated by the presence of a pale blue color. The resulting 2α-(2-carboxy-2-oxo-ethyl)-3β-hydroxy-5-oxo-1β-cyclopentaneheptanoic acid methyl ester, δ-lactone, 5-cyclic ethylene acetal (5A, $R_1=CH_3$) which is isolated but not purified is reacted with an acylating agent in the presence of an organic base. Preferred are acetylating agents as acetic anhydridic acetyl chloride, and the like, however, other acylating agents such as benzoyl chloride may be utilized. The reaction is worked up by techniques known to those skilled in the art yielding 2α-(2-acetoxy-2-carboxyvinyl)-3β-hydroxy-5-oxo-1β-cyclopentaneheptanoic acid methyl ester, δ-lactone, 5-cyclic ethylene acetal (6, $R_1=CH_3$, $R_4$=acetyl).

In the next step the above acyl compound is oxidized with osmium tetroxide in the presence of an alkali metal periodate in methanol. The compound is treated first with the osmium tetroxide until the solution darkens. The alkali metal periodate, preferably soduim periodate is then added portionwise over from 2 to 6 hours and the reaction stirred at about room temperature for from 2 to 6 hours, affording 2α-formyl-3β-[(methoxalyl)oxy]-5-oxo-1β-cyclopentaneheptanoic acid methyl ester, 5-cyclic ethylene acetal (7, $R_1=CH_3$).

A Wittig reaction is employed to form the octenone side chain at the 2-position of the cyclopentane ring. The formyl compound (7, $R_1=CH_3$) is treated with an alkali metal hydride and dimethyl 2-oxoheptylphosphonate in an anhydrous, inert solvent, such as tetrahydrofuran, dioxane, and the like. The intermediate 3β-[(methoxalyl)oxy]-2α-(3-oxo-1-octenyl)-5-oxo-1β-cyclopentaneheptanoic methyl ester, 5-cyclic ethylene acetal (7A, $R_1=CH_3$) is treated with a 1, 2-diamine such as ethylene diamine at from −10° to 25° C. for from 15 minutes to 2hours cleaving the 3β-methoxalyloxy group and affording 3β-hydroxy-2α-(3-oxo-1-octenyl)-5-oxo-1β-cyclopentaneheptanoic acid methyl ester, 5-cyclic ethylene acetal (8, $R_1=CH_3$, $R_5$=H).

The side chain keto group is reduced to a hydroxyl group with a mild reducing agent such as an alkali metal borohydride. The reduction is complete in from 15 minutes to 2 hours at from −20° to 25° C. The reaction affords a mixture of the R and S stereoisomers because both β-and α-hydroxy groups are formed, of which the α-hydroxy is preferred. The reaction mixture is chromatographed whereupon the isomers are separated and pure prostaglandin $E_1$ methyl ester-5-cyclic ethylene acetal [3β-hydroxy-2α-(3α-[S]-hydroxy-1-octenyl)-5-oxo-1β-cyclopentaneheptanoic acid methyl ester, 5-cyclic ethylene acetal, (9, $R_1=CH_3$, $R_5$=H)9 is obtained. The 3β[R]-hydroxy compound is separately obtained from the chromatographic column, and back oxidized by treatment with manganese dioxide to afford the keto starting material (8, $R_1=CH_3$, $R_5$=H) which can be recycled.

It is advantageous to employ the O-acyl, preferably the acetyl derivative of the 3β-hydroxyl group of compound 8 during the reduction and back oxidation of the side chain keto group. The acyl group has no deleterious effects on the reduction to the hydroxyl group. However, yields are considerably improved during the back-oxidation of the [R] hydroxyl group with manganese dioxide if the acyl group is present.

The final steps in this synthesis of racemic or optically active $PGE_1$ involves the removal of the protecting groups. The esters are hydrolized to the free acid using base-catalyzed hydrolysis in aqueous media. Preferred catalysts are alkali metal hydroxides such as potassium hydroxide in aqueous solution at from 0° to 40° C. for from 1 to 5 hours. The thus produced prostaglandin $E_1$-5-cyclic ethylene acetal (9, $R_1$=H, $R_5$=H) is treated with an aqueous acid preferably an organic acid such as acetic acid, at about room temperature for from 1 to 5 hours, cleaving the cyclic acetal and yielding prostaglandin $E_1$.

Depending on whether the starting material (compound 1) is racemic or optically active, racemic or optically active $PGE_1$ will be obtained. No loss in optical activity is observed when optically active (1) is employed; the reaction sequence (1) thru (10) being stereoselective and not tending to the racemization of any of the intermediates.

These are two series of optically active intermediates, one leading to (−) $PGE_1$ and the other to (+) $PGE_1$. The former is the naturally occurring form of $PGE_1$, and the one which possesses all of the biological activity. Both series of intermediates can be prepared using the procedures of the following examples. The series of intermediates leading to the naturally occurring $PGE_1$ is preferred and when referred to hereinbelow are termed "of the natural series."

The following examples are presented in order that the invention might be more readily understood. They should not be construed as being limitative of the invention.

Examples 1-P through 18-P describe the preparation of the starting material of the instant application and of the resolution of the intermediates into desired stereoisomer resulting in either the racemic (+) or optically active starting material viz $3\alpha,6,7,7\alpha$-tetrahydro-4-methyl-2-oxo-indaneheptanoic acid methyl ester.

EXAMPLE 1-P $3\alpha$-Methyl-4-cyclohexene-$1\alpha,2\alpha$-dimethanol

A solution of 25 g. of (+)-$3\alpha$-methyl-4-cyclohexene-$1\alpha,3\alpha$-dicarboxylic anhydride in 140 ml. of dry tetrahydrofuran is added to a suspension of 10.5 g. of lithium aluminum hydride in 140 ml. of tetrahydrofuran at such a rate as to maintain a gentle reflux. When the addition is complete the reaction mixture is refluxed for 3 hours and allowed to cool overnight. The complex is decomposed by the careful addition of 100 ml. of 1:1 tetrahydrofuran/water mixture to the reaction mixture at 0° C. 150 Ml. of chloroform is added, the reaction mixture is filtered, and the filter cake washed with chloroform. The combined filtrates are concentrated to dryness in vacuo. The residue is dissolved in benzene, dried with magnesium sulfate, and evaporated affording 22.4 g. of (+) $3\alpha$-methyl-4-cyclohexene-$1\alpha,2\alpha$-dimethanol as a colorless solid (m.p. 47–49.5°).

When in the above procedure the resolved acid/ester (−) $3\alpha$-methyl-4-cyclohexene-$1\alpha,2\alpha$-dicarboxylic acid 1-methyl ester is employed in place of $3\alpha$-methyl-4-cyclohexene-$1\alpha,3\alpha$-dicarboxylic anhydride there is obtained (−) $3\alpha$-methyl-4-cyclohexene-$1\alpha,2\alpha$-dimethanol $[\alpha]_D$ $CHCl_3$ −26°.

EXAMPLE 2-P $3\alpha$-Methyl-4-cyclohexene-$1\alpha,2\alpha$-dimethanol-di-p-toluenesulfonate To a solution of 10 g. (0.064 moles) of (+) $3\alpha$-methyl-4-cyclohexene-$1\alpha,2\alpha$-dimethanol in 30.4 g. of dry pyridine at −15° C. is added 26.83 g. (0.141 moles, 10% excess) of recrystallized p-toluenesulfonylchloride in portions at such a rate that the temperature does not exceed −5° C. The reaction mixture is stirred for 2 hours at −15° and stored overnight at 4° C. The reaction mixture is then poured slowly onto 250 cc of an ice/water mixture with stirring. The aqueous mixture is aged at 0° to 5° C. for 20 minutes and the aqueous layer decanted from the semisolid precipitate. The solid material is dissolved in chloroform and the chloroform solution is washed with dilute hydrochloric acid at 0° C., water, dilute aqueous potassium bicarbonate, water again, and finally with saturated aqueous sodium chloride. The chloroform solution is dried with magnesium sulfate and evaporated to dryness affording 27.7 g. of a viscous oil which crystallizes on dilution with ether. The product, (+) $3\alpha$-methyl-4-cyclohexene-$1\alpha,2\alpha$-dimethanol-di-p-toluene-sulfonate has a m.p. 62.5–65° C.

When in the above procedure (−) $3\alpha$-methyl-4-cyclohexene-$1\alpha,2\alpha$-dimethanol is employed in place of the racemic mixture there is obtained (−) $3\alpha$-methyl-4-cyclohexene-$1\alpha,2\alpha$-dimethanol di-p-toluene sulfonate; m.p. 52-54° C. $[\alpha]_D$ $CHCl_3$ −12°.

EXAMPLE 3A-P $3\alpha$-Methyl-4-cyclohexene-$1\alpha,2\alpha$-diactonitrile

A suspension of 1 g. of sodium cyanide and 10 ml. of dried dimethylsulfoxide is heated under nitrogen to 80–85° C. 2.37 G. of (+) $3\alpha$-methyl-4-cyclohexene-$1\alpha,2\alpha$-dimethanol di-p-toluenesulfonate is added in 3 portions over 15 minutes and the reaction mixture heated at 90–95° C. for 18 hours. The reaction mixture is cooled and diluted with 6 volumes of saturated sodium chloride solution. The aqueous mixture is extracted with methylene chloride, dried with magnesium sulfate, and evaporated to dryness in vacuo affording 0.781 g. of (+) $3\alpha$-methyl-4-cyclohexene-$1\alpha,2\alpha$-diacetonitrile which is obtained as an oil.

EXAMPLE 3B-P $3\alpha$-Methyl-4-cyclohexene-$1\alpha,2\alpha$-diacetonitrile A suspension of 14.7 g. of sodium cyanide and 140 ml. of dried dimethylsulfoxide is heated under nitrogen to 80–85°C. 27.7 g. of (+) $3\alpha$-methyl-4-cylclohexene-$1\alpha,2\alpha$-dimethanol di-p-toluenesulfonate is added in 3 portions over 15 minutes and the reaction mixture heated at 90–95°C. for 18 hours. The reaction mixture is cooled and diluted with 6 volumes of saturated sodium chloride solution. The aqueous mixture is extracted with methylene chloride; the extracts washed with saturated sodium chloride, dried with magnesium sulfate, and evaporated to dryness in vacuo affording 10.04 g. (96%) of (+) $3\alpha$-methyl-cyclohexene-$1\alpha,2\alpha$-diacetonitrile which is obtained as an oil.

When in the above procedure (−) $3\alpha$-methyl-4-cyclohexene-$1\alpha,2\alpha$-dimethanol di-p-toluenesulfonate is employed in place of the racemic mixture there is obtained (-) $3\alpha$-methyl-4-cyclohexene-$1\alpha,2\alpha$-diacetonitrile which is obtained as an oil.

EXAMPLE 4-P $3\alpha$-Methyl-4-cyclohexene-$1\alpha,2\alpha$-diacetic acid 81.7 G. of (+) $3\alpha$-methyl-4cyclohexene-$1\alpha,2\alpha$-diacetonitrile is suspended in 700 ml. of 33% aqueous potassium hydroxide and refluxed for 7 hours. After standing overnight at room temperature, the reaction mixture is treated with charcoal, extracted with ether, and acidified with concentrated HCl affording a solid precipitate weighing 92 g. The solid material is recrystallized from acetone/ethylacetate affording 67 g. of (+) 3α-methyl-4-cyclohexene-1α,2α-diacetic acid, m.p. 148–151°C.

When in the above procedure (−) 3α-methyl-4-cyclohexene-1α,2α-diacetonitrile is employed in place of the racemic mixture, there is obtained (−) 3α-methyl-4-cyclohexene-1α,2α-diacetic acid, m.p. 98.5–100°C., [α]$_D$ CHCl$_3$, −55°.

EXAMPLE 5-P

4α-Hydroxy-5β-iodo-3α-methyl-1α,2α-cyclohexanediacetic acid δ-lactone 12.8 G. of (+) 3α-methyl-4-cyclohexene-1α,2α-diacetic acid is dissolved in 150 ml. of water containing 36 g. of potassium bicarbonate. A solution of 30.68 g. of iodine and 65.21 g. of potassium iodide in 181 ml. of water is added with stirring. The reaction mixture is stirred for 3.5 hours in the dark, decolorized with saturated aqueous sodium bisulfite, acidified with 2.5 N hydrochloric acid, and extracted with ethyl acetate. The extracts are washed with an aqueous saturated sodium chloride solution containing a small amount of sodium bisulfite, and evaporated to dryness affording 20.04 g. of (+) 4α-hydroxy-5β-iodo-3α-methyl-1α,2α-cyclohexanediacetic acid δ-lactone m.p. 150°–152° C.

When in the above procedure (−) 3α-methyl-4-cyclohexenediacetic acid is employed in place of the racemic mixture, there is obtained (−) 4α-hydroxy-5β-iodo-3α-methyl-1α,2α-cyclohexanediacetic acid δ-lactone, m.p. 170°(dec) [α]$_D$ CHCl$_3$ -3°.

EXAMPLE 6-P

4α-Hydroxy-5β-iodo-3α-methyl-1α,2α-cyclohexanediacetic acid δ-lactone methyl ester 10.0 G. of (+) 4α-hydroxy-5β-iodo-3-methyl-1α,2α-cyclohexanediacetic acid δ-lactone is dissolved in the minimum amount of methanol and cooled to 0° C. Ethereal diazo methane is added dropwise maintaining the temperature at 10°C. or less until a yellow color persists in the reaction medium. The solvents are evaporated in vacuo and the residue recrystallized from ethanol affording (+) 4α-hydroxy-5β-iodo- 3α-methyl-1α,2α-cyclohexanediacetic acid δ -lactone methyl ester m.p. 80–82°C.

When in the above procedure (−) 4α-hydroxy-5β-iodo-3α-methyl-1α,2α-cyclohexanediacetic acid -δ-lactone is employed in place of the racemic mixture, there is obtained optically active 4α-hydroxy-5β-iodo-3α-methyl-1α,2α-cyclohexanediacetic acid δ-lactone, methyl ester an an oil.

EXAMPLE 7-P

4α-Hydroxy-3α-methyl-1α,2α-cyclohexanediacetic acid methyl ester, δ-lactone

To 68 G. of freshly prepared chromium diacetate dispersed in 250 ml. of dry dimethylsulfoxide containing 40 ml. of ethylmercaptan is added a solution of 20 g. of (+) 4α-hydroxy-5β-iodo-3α-methyl-1α,2α-cyclohexanediacetic acid δ-lactone methyl ester in 60 ml. of dimethylsulfoxide over 10 minutes. The reaction mixture is stirred at room temperature for 1¼ hours and diluted with 600 ml. of ice water. The reaction mixture is acidified with 250 ml. of 2.5 N hydrochloric acid. The solution is further diluted with 600 ml. of water and extracted with methylene-chloride. The combined extracts are washed with water until the extracts are colorless and then washed with saturated sodium chloride solution. The organic layer is dried with magnesium sulfate and evaporated to dryness. The residue is recrystallized from benzene affording 12.5 g. of (+) 4α-hydroxy-3α-methyl-1α,2α-cyclohexanediacetic acid methyl ester δ-lactone m.p. 83–84°C.

When in the above procedure (−) 4α-hydroxy-5β-iodo-3-methyl-1α,2α-cyclohexanediacetic acid, δ-lactone, methyl ester is employed in place of the racemic mixture there is obtained (−) 4α-hydroxy-3α-methyl-1α,2α-cyclohexanediacetic acid methyl ester, δ-lactone as an oil [α]$_D$ CHCl$_3$ -48°.

EXAMPLE 8-P

4α-Hydroxy-3α-methyl-1α,2α-cyclohexanediacetic acid δ-lactone

32 G. (0.14 moles) of (+) 4α-hydroxy-3α-methyl-1α,2α-cyclohexanediacetic acid methyl ester, δ-lactone is saponified by stirring under nitrogen at room temperature for 1 hour with 15.84 g. (0.28 moles) of potassium hydroxide in 283 ml. of water. The resulting solution is extracted with ether, acidified with 2.5 N hydrochloric acid, and extracted with ethyl acetate. The combined extracts are washed with aqueous Na$_2$S$_2$O$_3$ solution, and saturated sodium chloride solution, and dried over magnesium sulfate. The organic solution is evaporated to dryness affording 27.52 g. of (+) 4α-hydroxy-3α-methyl-1α,2α-cyclohexanediacetic acid δ-lactone m.p. 135–139°. Following recrystallization from an acetone/ether mixture, the m.p. is raised to 138–140° C.

When in the above procedure (−) 4α-hydroxy-3α-methyl-1α,2α-cyclohexanediacetic acid methyl ester, δ-lactone is employed in place of the racemic mixture there is obtained (−) 4α-hydroxy-3αmethyl-1α,2α-cyclohexanediacetic acid, δ-lactone m.p. 118–120.5° C., [α]$_D$ CHCl$_3$ -55°.

EXAMPLE 9-P

4α-Hydroxy-3α-methyl-1α,2α-cyclohexanediacetic acid

A mixture of 7.0 g. of (+) 4α-hydroxy-3α-methyl-1α,2α-cyclohexanediacetic acid δ-lactone in 70 ml. of water with 14 g. of potassium hydroxide is heated on a steam bath under nitrogen for 2.5 hours. The gaseous carbon dioxide is passed through the solution until the pH is 8.0. The reaction mixture is then acidified to a pH of 2 with dilute hydrochloric acid and extracted with ethyl acetate affording 8.32 g. of (+) 4α-hydroxy-3α-methyl-1α,2α-cyclohexanediacetic acid m.p. 151–153° C.

When in the above procedure (−) 4α-hydroxy-3α-methyl-1α,2α-cyclohexanediacetic acid, δ-lactone is employed in place of the racemic mixture, there is obtained (−) 4α-hydroxy-3α-methyl-1α,2α-cyclohexanediacetic acid [α]$_D$ CHCl$_3$ -66°.

EXAMPLE 10-P

4α-hydroxy-3α-methyl-1α,2α-cyclohexanediacetic acid dimethyl ester

Following the procedure of Example 6 employing 10.0 g. of (+) 4α-hydroxy-3α-methyl-1α,2α-cyclohexanediacetic acid there is obtained (+) 4α-hydroxy-3α-methyl-1α,2α-cyclohexanediacetic acid dimethyl ester.

When in the above procedure (−) 4α-hydroxy-3α-methyl-1α,2α-cyclohexanediacetic acid is employed in place of the racemic mixture there is obtained (−) 4α-hydroxy-3α-methyl-1α,2α-cyclohexanediacetic acid dimethyl ester.

EXAMPLE 11-P

4α-Hydroxy-3α-methyl-1α,2α-cyclohexanediacetic acid dimethyl ester methanesulfonate To a stirred solution of 28.95 ml. of methane sulfonyl chloride in 50 ml. of dry pyridine at 0°C. is added a solution of 11 g. of 4α-hydroxy-3α-methyl-1α,2α-cyclohexanediacetic acid dimethyl ester in 86 ml. of dry pyridine dropwise. The reaction mixture is stirred for ½ hour at 0° C. and allowed to stand overnight at 0°C. The reaction is poured onto ice-water and extracted with chloroform. The combined extracts are acidified with dilute HCl at 0° C. and washed with water, potassium bicarbonate solution, water, and saturated sodium chloride solution. The organic layer is dried with magnesium sulfate and evaporated to dryness affording 14.4 g. of 4α-hydroxy-3α-methyl-1α,2α-cyclohexanediacetic acid dimethyl ester methanesulfonate obtained as an oil.

EXAMPLE 12-P

3-Methyl-3-cyclohexene-1α,2α-diacetic acid dimethyl ester

A solution of 14 g. of 4α-hydroxy-3α-methyl-1α,2α-cyclohexanediacetic acid dimethyl ester methanesulfonate is 168 ml. of dry dimethyl sulfoxide is heated at 102–104° C. under nitrogen with stirring for 6¼ hours. The reaction mixture is cooled, combined with ice water, and extracted with hexane. The combined extracts are washed successively with 4 portions of water and 1 portion of saturated sodium chloride solution. The hexane layer is dried with magnesium sulfate and evaporated to dryness in vacuo affording 8.5 g. of (+) 3-methyl-3cyclohexene-1α,2α-diacetic acid dimethyl ester obtained as an oil.

EXAMPLE 13-P

3-Methyl-3-cyclohexene-1α,2α-diacetic acid dimethyl ester 7.667 of (+) 4α-hydroxy-3α-methyl-1α,2α-cyclohexanediacetic acid dimethyl ester in 16 ml. of dry benzene is added dropwise, at 0°, to a stirred solution of 3.95 g. of methanesulfonyl chloride in 77 ml. of dry pyridine. After storing the mixture overnight at 0°, it is stirred at room temperature for 6 hours followed by heating at 100–105°for 16 hours. The mixture is well chilled, diluted with hexane and acidified to pH with 6 N hydrochloric acid. After separation of the two phases the aqueous layer is reextracted with hexane-benzene mixture. The combined extracts are washed with water, potassium bicarbonate solution, and saturated sodium chloride solution, and dried over magnesium sulfate. The solution is evaporated to dryness affording 6.78 g. of (+) 3-methyl-3-cyclohexene-1α,2α-diacetic acid dimethyl ester as an oil.

When in Examples 11 and 13 (−) 4α-hydroxy-3α-methyl-1α,2α-cyclohexanediacetic acid, dimethyl ester is employed in place of the racemic mixture there is obtained (−) 3-methyl-3-cyclohexene-1α,2α-diacetic acid dimethyl ester as an oil.

EXAMPLE 14-P

3-Methyl-3-cyclohexene-1α,2α-diacetic acid

A mixture of 0.2403 g. of (+) 3-methyl-3-cyclohexane-1α,2α-diacetic acid dimethyl ester, 2 ml. of methanol, 2.5 ml. of water, and 0.48 g. of potassium hydroxide is stirred under nitrogen at room temperature overnight. Excess methanol is removed in vacuo and the basic aqueous medium extracted with ether, cooled, acidified with 2.5 N hydrochloric acid, to pH 4 salted out, and extracted with ethyl acetate. Combined extracts after washing with saturated sodium chloride solution, drying over magnesium sulfate and evaporating to dryness afforded 0.1894 g. of solid acid, which on recrystallization from ether-hexane mixture had m.p. 121–122.5° C.

When in the above procedure (−) 3-methyl-4-cyclohexene-1α,2α-diacetic acid, dimethyl ester is employed in place of the racemic mixture there is obtained (−) 3-methyl- 3-cyclohexene-1α,2α-diacetic acid m.p. 102.5–104° C. $[\alpha]_D$ CHCl$_3$ -99.6°.

The above (+) or (−) diacid is converted to the corresponding diester using the procedure of Example 6.

EXAMPLE 15-P

3α,6,6,7α-Tetrahydro-1α-(methoxycarbonyl)-4methyl-2-oxoindaneheptanoic acid methyl ester Under an anhydrous and inert atmosphere 36.83 ml. of 0.565 M potassium-t-butoxide in dry t-butanol is evaporated to a white powdery residue under reduced pressure. The dry powder is dispersed in 50 ml. of dry xylene. 5 G. of (+) 3-methyl-3-cyclohexene-1α,2α-diacetic acid dimethyl ester in 40 ml. of xylene is added to the above dispersion dropwise. The reaction mixture is brought to reflux with the simultaneous removal by distillation of the lower boiling components. Refluxing at the temperature of boiling xylene is then continued for 2 hours. 45 ml. of excess xylene is distilled off and 6.18 g. (10% molar excess) of methyl-7-iodoheptanoate in 5 ml. of xylene is added. The reaction mixture is refluxed for 16 hours, cooled, and diluted with benzene. Solid potassium iodide is removed by filtration recovering 99% of theory. The clear organic filtrate is washed with saturated sodium chloride, dried over magnesium sulfate, and evaporated to dryness affording 7.3 g. of 3α,6,7,7α-tetrahydro-1-(methoxycarbonyl)-4-methyl-2-oxoindaneheptanoic acid methyl ester which is used as is in the next reaction.

When in the above procedure (−) 3-methyl-3-cyclohexene-1α,2α-diacetic acid dimethyl ester is employed in place of the racemic mixture there is obtained (−) 3α,6,7,7α-tetrahydro-1α-(methoxycarbonyl)-4methyl-2-oxoindaneheptanoic acid methyl ester.

EXAMPLE 16-P

3α,6,6,7α-tetrahydro-4-methyl-2-oxo-1β-indaneheptanoic acid methyl ester

A stirred mixture of 7.3 g. of (+) 3α,6,7,7α-tetrahydro-1α-(methoxycarbonyl)-4-methyl-2oxoindaneheptanoic acid methyl ester and 21.27 g. of lithium iodide dihydrate in 120 ml. of s-collidine under a nitrogen atmosphere is refluxed for 11 hours. The reaction mixture is evaporated and concentrated in a high vacuum to remove the s-collidine. The residue is dispersed in ethyl acetate and acidified with 2.5 N hydrochloric acid and salted out with solid sodium chloride. The organic layer is separated and washed with saturated sodium chloride solution. The combined aqueous layers are reextracted with ethyl acetate and the combined ethyl acetate extracts dried over a magnesium sulfate affording the heptanoic acid intermediate. The acid is dissolved in a minimum amount of methanol and treated with excess ethereal diazomethane as in Example 6 affording 6.5 g. of (+) 3α,6,7,7α-tetrahydro-4methyl-2-oxo-1β-indaneheptanoic acid methyl ester.

When in the above procedure (−) 3α,6,7,7α-tetrahydro-1α-(methoxycarbonyl)-4-methyl-2oxoindaneheptanoic acid, methyl ester is employed in place of the racemic mixture there is obtained (+) 3α,6,7,7α-tetrahydro-4-methyl-2-oxo-1β-indaneheptanoic acid, methyl ester $[\alpha]_D$ CHCl$_3$ +11.6°.

EXAMPLE 17-P

Resolution of 3α-methyl-4-cyclohexene-1α-2α-dicarboxylic acid-1-methyl ester 4.98 G. (0.03 moles) of (+) 3α-methyl-4-cyclohexene-1α,2α-dicarboxylic anhydride is dissolved in 100 ml. of anhydrous methanol and cooled to 0° C. The reaction mixture is treated with 20 ml. of 1.35 N sodium methoxide in methanol. The methanol is evaporated in vacuo, the residue is acidified with sodium dihydrogen phosphate, and the (+) 3α-methyl-4-cyclohexene-1α,2α-dicarboxylic acid-1-methyl ester extracted with ether, dried, evaporated, and recrystallized from ether yielding 3.15 g. m.p. 110–112°C. The acid ester is resolved by treating 0.594 g. (0.003 moles) in 10 ml. of ether with 0.856 g. of (+) dehydroabietylamine in 10 ml. of ether. The precipitated solid is recrystallized from acetone affording 0.53 g. of a salt m.p. 163–165°C. The salt is converted to the free acid by extracting a suspension of the salt in ether/ethyl acetate with aqueous sodium bicarbonate. The aqueous solution of the sodium salt of the acid is treated with sodium dihydrogen phosphate precipitating the free acid. The solid material is dried affording (−) 3α-methyl-4-cyclohexene-1α,2α-dicarboxylic acid-1-monomethyl ester m.p. 60–61° C. $[\alpha]_D$ CHCl$_3$ -69°.

The mother liquor of the initially precipitated salt is concentrated causing the additional precipitation of a salt m.p. 143–145° C. which on treatment above afforded (+) 3α-methyl- 4-cyclohexene-1α,2α-dicarboxylic acid-1-monomethyl ester $[\alpha]_D$ CHCl$_3$ +67.7°.

The above acid ester is reduced following the procedure of Example 1 affording 3-methyl-4-cyclohexene-1α,2α-dimethanol in optically active form.

EXAMPLE 18-P

Resolution of 4α-hydroxy-3α-methyl-1α,2α-cyclohexanediacetic acid δ-lactone 53.95 G. of (+) 4α-hydroxy-3α-methyl-1α,2α-cyclohexanediacetic acid δ-lactone is dissolved in the minimum amount of chloroform (150 ml.) and a solution of 79 g. of (+) dehydroabietylamine in 300 ml. of benzene is added. Crystallization occurs overnight yielding 59.94 g. of fine crystals m.p. 158–167°C. Partial concentration of the mother liquor and dilution with ether yields a second crop of 26.7 g. of crystals m.p. 144–148°C. Recrystallization of the second crop of crystals from methanol/ether affords 20.1 g. of fine crystals m.p. 148°–150° C. The recrystallized salt is suspended in ethyl acetate and extracted with aqueous potassium bicarbonate solution. The aqueous extract is washed with ether, acidified with 2.5 N Hydrochloric acid, saturated with sodium chloride, and the free optically active 4α-hydroxy-3α-methyl-1α,2α-cyclohexanediacetic acid δ-lactone is extracted with ethyl acetate. The extracts are washed with a saturated sodium chloride solution, dried over magnesium sulfate, and evaporated to dryness, affording of crystalline (−) 4α-hydroxy-3α-methyl-1α,2α-cyclohexanediacetic acid, δ-lactone m.p. 118°–120.5° C. $[\alpha]_D$ CHCl$_3$ -54.7°.

The first crop of salt crystals may also be recrystallized affording 37.77 g. of crystals m.p. 169°–170.5° C. This salt is treated in a similar manner as above affording (+) 4α-hydroxy-3α-methyl-1α,2α-cyclohexanediacetic acid, δ-lactone m.p. 118°–120.5° C. $[\alpha]_D$ CHCl$_3$ +55°.

EXAMPLE 1

3α,6,7,7α-tetrahydro-4-methyl-2-oxo-1β-indaneheptanoic acid methyl ester, 2-cyclic ethylene acetal A mixture of 11.8 g. of (+)-3α,6,7,7α-tetrahydro-4-methyl-2-oxo-1β-indaneheptanoic acid methyl ester, 27 ml. of ethylene glycol and 300 mg. of p-toluene sulfonic acid mono-hydrate in 600 ml. of benzene is refluxed with stirring for 18 hours using a Dean-Stark trap to separate the water formed in the reaction. The reaction mixture is cooled and added to 300 ml. of cold 5% potassium bicarbonate. The layers are separated and the aqueous layer extracted twice with 2:1 benzene-hexene. The combined organic fractions are washed 3 times with saturated aqueous sodium chloride, dried over sodium sulfate and evaporated to dryness affording 12.6 g. of (+)-3α,6,7,7α-tetrahydro-4-methyl-2-oxo-1β-indaneheptanoic acid methyl ester, 2-cyclic ethylene acetal; nmr (C$_6$D$_6$)δ3.56 [4H-ethylene group].

When in the above procedure (+)-3α,6,7,7α-tetrahydro-4-methyl-2-oxo-1β-indaneheptanoic acid methyl ester $[a]_D^{CHCl_3}$ + 11.6° is employed in place of the racemic mixture there is obtained optically active-3α,6,7,7α-tetrahydro-4-methyl-2-oxo-1β-indaneheptanoic acid methyl ester, 2-cyclic acetal $[a]_D^{CHCl_3}$ − 26°.

EXAMPLE 2

3β-Acetyl-2α-(2-methoxycarbonylethyl)-5-oxo-1β-cyclopentaneheptanoic acid methyl ester, 5-cyclic ethylene acetal

A.

3-Acetyl-2α-(2-carboxyethyl)-5-oxo-1β-cyclopentaneheptanoic acid methyl ester, 5-cyclic ethylene acetal To a stirred solution of 5.69 g. of (+)-3α,6,7,7α-tetrahydro-4-methyl-2-oxo-1β-indaneheptanoic acid methyl ester, 2-cyclic ethylene acetal in 410 ml. of t-butanol and 11 ml. of water is added a mixture of 5.80 g. of potassium carbonate, 22'8 g. of sodium periodate, and 270 mg. of potassium permanganate in 1230 ml. of water. The reaction mixture is stirred at 20°–25° C. for 20 hours and concentrated in vacuo to remove the t-butanol. Ethylene glycol (0.5 ml.) is added and the reaction mixture extracted with 1:1 etherbenzene to remove neutral material. The agueous layer is acidified with solid sodium dihydrogen phosphate and extracted 4 times with 1:1 ethyl acetate-benzene. The organic layer is dried over sodium sulfate and evaporated to dryness in vacuo affording (+)-3-acetyl-2α-(2-carboxyethyl)-5-oxo-1β-cyclopentaneheptanoic acid methyl ester, 5-cyclic ethylene acetal as a mixture of the 3α and 3β isomers.

B.
3β-Acetyl-2α-(2-methoxycarbonylethyl)-5-oxo-1β-cyclopentaneheptanoic acid methyl ester, 5-cyclic ethylene acetal The above (+)-3-acetyl-2α-(2-carboxyethyl)-5-oxo-1β-cyclopentaneheptanoic acid methyl ester, 5-cyclic ethylene acetal is dissolved in 10 ml. of ether and treated with ethereal diazomethane until an excess is present as indicated by a persistent yellow color. After 5 minutes the reaction mixture is evaporated to dryness in vacuo and the residue dissolved in 20 ml. of methanol and 2 ml. of 1N sodium methoxide in methanol is added. The reaction mixture is stirred for 18 hours at room temperature and added to cold saturated aqueous sodium dihydrogen phosphate. The methanol is removed in vacuo and the mixture extracted with 1:1 ethyl acetate-benzene. The organic extract is dried over sodium sulfate and evaporated to dryness affording (+)-3β-acetyl-2α-(2-methoxycarbonylethyl)-5-oxo-1β-cyclopentaneheptanoic acid methyl ester, 5-cyclic ethylene acetal, nmr (CDCl$_3$) δ2.13 [3H-CH$_3$CO].

When in the above procedures (−)-3α,6,7,7α-tetrahydro-4-methyl-2-oxo-1β-indaneheptanic acid methyl ester, 2-cyclic ethylene acetal is employed in place of the racemic compound there is obtained (+)-3β-acetyl-2α-(2-methoxycarbonylethyl)-5-oxo-1β-cyclopentaneheptanoic acid, methyl ester, 5-cyclic ethylene acetal, $[\alpha]_D^{CHCl_3}$ + 6.8°.

EXAMPLE 3
3β-Acetoxy-2α-(2-methoxycarbonylethyl)-5-oxo-1β-cyclopentaneheptanoic acid methyl ester, 5-cyclic ethylene acetal 60 G. of solid disodium monohydrogen phosphate is added to a stirred solution of 4.50 g. of (+)-3β-acetyl-2α-[2-methoxycarbonylethyl]-5-oxo-1β-cyclopentaneheptanoic acid methyl ester, 5-cyclic ethylene acetal in 25 ml. of methylene chloride and the mixture cooled to 0° C. 45 Ml. of freshly prepared 0.3M trifluoroperacetic acid in methylene chloride is added and the reaction mixture stirred for 18 hours at room temperature. A thin layer chromatogram of an aliquot portion of the reaction mixture indicates the reaction to be about 60% complete. An addition 40 ml. of the 0.3M trifluoroperacetic acid in methylene chloride is added. After stirring an additional 24 hours the reaction is complete. The reaction is filtered, the precipitate washed with methylene chloride and the combined filtrates washed with cold aqueous potassium iodide and cold aqueous sodium thiosulfate to remove residual peracid. The organic extract is washed with water, dilute aqueous potassium bicarbonate and saturated aqueous sodium chloride. The organic layer is dried over sodium sulfate and evaporated to dryness in vacuo affording (+)-3β-acetoxy-2α-(2-methoxycarbonylethyl)-5-oxo-1β-cyclopentaneheptanoic acid methyl ester, 5-cyclic ethylene acetal as a colorless oil, nmr (CDCl$_3$) δ2.01 [3H-CH$_3$COO].

When in the above procedure (+)-3β-acetyl-2α-(2-methoxycarbonylethyl)-5-oxo-1β-cyclopentaneheptanoic acid methyl ester, 5-cyclic ethylene acetal is employed in place of the racemic mixture there is obtained optically active 3β-acetoxy-2α-(2-methoxycarbonylethyl)-5-oxo-1β-cyclopentaneheptanoic acid methyl ester, 5-cyclic ethylene acetal, of the natural series.

EXAMPLE 4
2α-(2-Carboxyethyl)-3β-hydroxy-5-oxo-1β-cyclopentaneheptanoic acid methyl ester, δ-lactone, 5-cyclic ethylene acetal

A.
2α-(2-methoxycarbonylethyl)-3β-hydroxy-5-oxo-1β-cyclopentaneheptanoic acid methyl ester, 5-cyclic ethylene acetal 6 Ml. of 1.00N sodium methoxide is added to a stirred solution of 4.25 g. of (+)-3β-acetoxy-2α-(2-methoxycarbonylethyl)-5-oxo-1β-cyclopentaneheptanoic acid methyl ester, 5-cyclic ethylene acetal in 25 ml. of methanol under a nitrogen atmosphere and stirred at room temperature for 2 hours. The reaction mixture is poured into excess cold saturated aqueous sodium dihydrogen phosphate and extracted with 1:1 ethyl acetate-benzene. The organic extract is dried over sodium sulfate and evaporated to dryness in vacuo. The residue is purified chromatographically employing 180 g. of silica gel and eluting with 25% acetone in chloroform affording pure (+)-2α-(2-methoxycarbonylethyl)-3β-hydroxy-5-oxo-1β-cyclopentaneheptanoic acid methyl ester, 5-cyclic ethylene acetal.

When in the above procedure optically active-3β-acetoxy-2α-(2-methoxycarbonylethyl)-5-oxo-1β-cyclopentaneheptanoic acid methyl ester, 5-cyclic ethylene acetal of the natural series is employed in place of the racemic mixture there is obtained (+)-2α-(2-methoxycarbonylethyl)-3β-hydroxy-5-oxo-1β-cyclopentaneheptanoic acid methyl ester, 5-cyclic ethylene acetal $[\alpha]_D^{CHCl_3}$ + 14.7°.

B.
2α-(2-Carboxyethyl)-3β-hydroxy-5-oxo-1β-cyclopentaneheptanoic acid methyl ester, δ-lactone, 5-cyclic ethylene acetal 1.66 G. (+)-2α-(2-methoxycarbonylethyl)-3β-hydroxy-5-oxo-1β-cyclopentaneheptanoic acid methyl ester, 5-cyclic ethylene acetal is dissolved in 350 ml. of benzene in a nitrogen atmosphere and rendered anhydrous by removing 30 ml. of benzene by distillation. 0.25 Ml. of 0.66M potassium t-butoxide in t-butanol is added and an additional 140 ml. of benzene removed by distillation over a period of 4 hours. The reaction mixture is cooled, added to cold saturated aqueous sodium dihydrogen phosphate, and extracted with benzene. The combined organic layers are washed with saturated aqueous sodium chloride, dried over sodium sulfate, and evaporated to dryness in vacuo affording (+)-2α-(2-carboxyethyl)-3β-hydroxy-5-oxo-1β-cyclopentaneheptanoic acid methyl ester, δ-lactone 5-cyclic ethylene acetal as a pale yellow oil.

When in the above procedure (+)-2α-(2-methoxycarbonylethyl-3β-hydroxy-5-oxo-1β-cyclopentaneheptanoic acid methyl ester, 5-cyclic ethylene acetal is employed in place of the racemic mixture there is obtained optically active 2α-(2-carboxyethyl)-3β-hydroxy-5-oxo-1β-cyclopentaneheptanoic acid methyl ester, δ-lactone 5-cyclic ethylene acetal of the natural series.

EXAMPLE 5

2α-(2-carboxy-2-formylethyl)-3β-hydroxy-5-oxo-1β-cyclopentaneheptanoic acid methyl ester, δ-lactone 5-cyclic ethylene acetal 210 Mg. of 50% sodium hydride dispersion is added to a stirred solution of 1.36 g. of (+)-2α-(2-carboxyethyl)-3β-hydroxy-5-oxo-1β-cyclopentaneheptanoic acid methyl ester, δ-lactone, 5-cyclic ethylene acetal in 25 ml. of methyl formate under a nitrogen atmosphere over a period of 3 minutes at 0° C. The reaction mixture is stirred for 1 hour at 0° C. and 4 hours at 20° C. The solvent is removed in vacuo and the residue triturated with ether and the precipitate filtered and washed with ether. The precipitate is dissolved in cold saturated aqueous sodium dihydrogen phosphate, extracted with ethyl acetate, dried over sodium sulfate and evaporated to dryness. The residue is crystallized from ether-hexane affording (+)-2α-(2-carboxy-2-formylethyl)-3β-hydroxy-5-oxo-1β-cyclopentaneheptanoic acid methyl ester, δ-lactone, 5-cyclic ethylene acetal, m.p. 88°–90° C.

When in the above procedure optically active-2α-(2-carboxyethyl)-3β-hydroxy-5-oxo-1β-cyclopentaneheptanoic acid methyl ester, δ-lactone 5-cyclic ethylene acetal of the natural series is employed in place of the racemic mixture, there is obtained optically active 2α-(2-carboxy-2-formylethyl)-3β-hydroxy-5-oxo-1β-cyclopentaneheptanoic acid methyl ester, δ-lactone, 5-cyclic ethylene acetal, of the natural series, m.p. 80°–81°.

EXAMPLE 6

2α-(2-acetoxy-2-carboxyvinyl)-3β-hydroxy-5-oxo-1β-cyclopentaneheptanoic acid methyl ester, δ-lactone 5-cyclic ethylene acetal

A.

2β-(2-carboxy-2-oxoethyl)-3β-hydroxy-5-oxo-1β-cyclopentaneheptanoic acid methyl ester, δ-lactone, 5-cyclic ethylene acetal A solution of 460 mg. of (+)-2α-(2-carboxy-2-formylethyl)-3β-hydroxy-5-oxo-1β-cyclopentaneheptanoic acid methyl ester, δ-lactone 5-cyclic ethylene acetal in 6 ml. of methylene chloride and 4.4 ml. of pyridine is cooled to −70° C. and treated with a 5% ozone-oxygen mixture until an excess of ozone is present as indicated by a persistent pale blue color. The excess ozone is evaporated by bubbling nitrogen into the reaction and the solvents are removed in vacuo. The residue is triturated with ether affording crystalline (+)-2α-(2-carboxy-2-oxoethyl)-3β-hydroxy-5-oxo-1β-cyclopentaneheptanoic acid methol ester, δ-lactone, 5-cyclic ethylene acetal, m.p. 114°–116° C.

B.

2α-(2-acetoxy-2-2-carboxyvinyl)-3β-hydroxy-5-oxo-1β-cyclopentaneheptanoic acid methyl ester, δ-lactone, 5-cyclic ethylene acetal The ozonolysis product is acetylated in 6 ml. of pyridine and 3 ml. of acetic anhydride at room temperature for 17 hours. 6 Ml. of xylene is added and the reaction mixture evaporated to dryness in vacuo. The residue is triturated with ether-hexane affording crystalline (+)-2α-(2-acetoxy-2-carboxyvinyl)-3β-hydroxy-5-oxo-1β-cyclopentaneheptanoic acid methyl ester, δ-lactone, 5-cyclic ethylene acetal m.p. 82°–84° C.

When in the above procedure optically activate-2α-(2-carboxy-2-formylethyl)-3β-hydroxy-5-oxo-1β-cyclopentaneheptanoic acid methyl ester, δ-lactone, 5-cyclic ethylene acetal is employed in place of the racemic mixture, there is obtained (+)-2α-(2-acetoxy-2-carboxyvinyl)-3β-hydroxy-5-oxo-1β-cyclopentaneheptanoic acid methyl ester, δ-lactone, 5-cyclic ethylene acetal $[\alpha]_D^{CHCl_3} + 30°$ of the natural series.

EXAMPLE 7

2α-formyl-3β-[(methoxalyl)oxy]-5-oxo-1β-cyclopentaneheptanoic acid methyl ester, 5-cyclic ethylene acetal 14. Mg. of osmium tetroxide in 1.4 ml. of methanol is added to a stirred solution of 430 mg. of (+)-2α-(2-acetoxy-2-carboxyvinyl)-3β-hydroxy-5-oxo-1β-cyclopentaneheptanoic acid methyl ester, δ-lactone, 5-cyclic ethylene acetal in 16 ml. of methanol. The reaction mixture darkens in 10–15 minutes and 440 mg. of powdered sodium periodate is added portionwise over 3 hours. The reaction mixture is stirred for 1 additional hour, filtered, and the filtrate evaporated to dryness in vacuo. The residue is dissolved in 2.5 ml. of 1:1 ethyl acetate-benzene and the solution washed with water and saturated aqueous sodium chloride. The organic layer is dried over sodium sulfate and evaporated to dryness in vacuo affording (+)-2α-formyl-3β-[(methoxalyl)oxy]-5-oxo-1β-cyclopentanehptanoic acid methyl ester, 5-cyclic ethylene acetal as an oil.

When in the above procedure (+)-2α-(2-acetoxy-2-carboxyvinyl)-3β-hydroxy-5-oxo-1β-cyclopentaneheptanoic acid methyl ester, δ-lactone, 5-cyclic ethylene acetal is employed in place of the racemic mixture, there is obtained optically active-2α-formyl-3β-[(methoxalyl)oxy]-5-oxo-1β-cyclopentaneheptanoic acid methyl ester, 5-cyclic ethylene acetal, of the natural series.

EXAMPLE 8

3β-Hydroxy-2α-(3-oxo-1-octenyl)-5-oxo-1β-cyclopentaneheptanoic acid methyl ester, 5-cyclic ethylene acetal

A.

3β-[(methoxalyl)oxy]-2α-(3-oxo-1-octenyl)-5-oxo-1β-cyclopentaneheptanoic acid methyl ester, 5-cyclic ethylene acetal 230 Mg. of dimethyl-2-oxoheptyl phosphonate in 4 ml. of tetrahydrofuran is added to a stirred suspension of 50 mg. of 50% sodium hydride dispersion in 10 ml. of tetrahydrofuran under a nitrogen atmosphere at 0° C. The reaction mixture is stirred at 0° C. for 30 minutes and a solution of 420 mg. of (+)-2α-formyl-3β-[(methoxalyl)oxy]-5-oxo-1β-cyclopentaneheptanoic acid methyl ester, 5-cyclic ethylene acetal in 4 ml. of tetrahydrofuran is added dropwise over 5 minutes. After 10 minutes the mixture is allowed to warm to room temperature and stirred for 2 hours. The reaction is cooled to 10° C., added to cold saturated aqueous sodium dihydrogen phosphate and extracted with ethyl acetate. The organic extract is washed with saturated aqueous sodium chloride, stirred over sodium sulfate, and evaporated to dryness in vacuo affording (+)-3β-[(methoxalyl)oxy]-2α-(3-oxo-1-octenyl)-5-oxo-1β-cyclopentaneheptanoic acid methyl ester, 5-cyclic ethylene acetal containing a smaller amount of (+)-3β-hydroxy-2α-(3-oxo-1-octenyl)-5-oxo-1β-cyclopentaneheptanoic acid methyl ester, 5-cyclic ethylene acetal.

B.

3β-Hydroxy-2α-(3-oxo-1-octenyl)-5-oxo-1β-cyclopentaneheptanoic acid methyl ester, 5-cyclic ethylene acetal The above mixture is dissolved in 7.5 ml. of methanol and 60 ml. of ethylenediamine in 5 ml. of methanol added dropwise at 0° C. The reaction mixture is stirred for 45 minutes at 20° C. and the solvent removed in vacuo. The residue is partitioned between ethyl acetate and saturated aqueous sodium dihydrogen phosphate. The layers are separated and the aqueous layer extracted with ethyl acetate. The combined extracts are dried and evaporated to dryness in vacuo. The residue is chromatographed on 35 g. of silica gel eluting with 30% acetone and chloroform taking 40 fractions of 4 ml. each. Fractions 5–14 are combined and evaporated to dryness in vacuo affording 250 mg. of pure (+)-3β-hydroxy-2α-(3-oxo-1-octenyl)-5-oxo-1β-cyclopentaneheptanoic acid methyl ester, 5-cyclic ethylene acetal, λmax., (methanol)=232nm (E12,500).

When in the above procedure, optically active-3β-[(methoxalyl)oxy]-5-oxo-1β-cyclopentaneheptanoic acid methyl ester, 5-cyclic ethylene acetal of the natural series is employed in place of the racemic mixture, there is obtained optically active-(3β-hydroxy-2α-(3-oxo-1-octenyl)-5-oxo-1β-cyclopentaneheptanoic acid methyl ester, 5-cyclic ethylene acetal.

EXAMPLE 9

Prostaglandin $E_1$, methyl ester, cyclic ethylene acetal. [3β-hydroxy-2α-(3 [S]-hydroxy-1-octenyl)-5-oxo-1β-cyclopentaneheptanoic acid methyl ester, 5-cyclic ethylene acetal]

23 Mg. of sodium borohydride in 2 ml. of methanol at −10° C is added dropwise to a stirred solution of 245 mg. of (+)-3β-hydroxy-2α-(3-oxo-1-octenyl)-5-oxo-1β-cyclopentaneheptanoic acid methyl ester, 5-cyclic ethylene acetal in 6 ml. of methanol at −10° C. The reaction mixture is stirred for 40 minutes at −10° C. and added to 50 ml. of saturated sodium dihydrogen phosphate and extracted with ethyl acetate. The extracts are washed with saturated aqueous sodium chloride, dried over sodium sulfate, and evaporated to dryness in vacuo. The residue is chromatographed on 20 g. of silica gel eluting with 50% acetone-chloroform and collecting 50 fractions of 3 ml. each. Fractions 8–18 are combined and evaporated to dryness affording (+)-3β-hydroxy-2α-(3[R]hydroxy-1-octenyl)-5-oxo-1β-cyclopentaneheptanoic acid methyl ester, 5-cyclic ethylene acetal. The 3β[R]isomer (100 mg.) is dissolved in 5 ml. of ethyl acetate and stirred with 2 g. of activated maganese dioxide for 6 hours. The mixture is filtered, the precipitate washed with acetone and the combined filtrates and washings evaporated to dryness in vacuo affording recyclicable (+)-3β-hydroxy-2α-(3-oxo-1-octenyl)-5-oxo-1β-cyclopentaneheptanoic acid methyl ester, 5-cyclic ethylene acetal.

Fractions 21–25 are combined and evaporated to dryness affording (+)-3β-hydroxy-2α-(3 [S]-hydroxy-1-octenyl)-5-oxo-1β-cyclopentaneheptanoic acid methyl ester, 5-cyclic ethylene acetal m.p. 54°–56° C.

When in the above procedure optically active-3β-hydroxy-2α-(3-oxo-1-octenyl)-5-oxo-1β-cyclopentaneheptanoic acid methyl ester, 5-cyclic ethylene acetal is employed in place of the racemic mixture, there is obtained optically active prostaglandin $E_1$, methyl ester, cyclic ethylene acetal, [3β-hydroxy-2α-(3 [S]-hydroxy-1-octenyl)5-oxo-1β-cyclopentaneheptanoic acie methyl ester, 5-cyclic ethylene acetal] of the natural series, m.p. 48°–51° C.

EXAMPLE 10

Prostaglandin $E_1$, cyclic ethylene acetal.

[3β-hydroxy-2α-(3 [S]hydroxy-1-octenyl)-5-oxo-1β-oxocyclopentaneheptanoic acid, 5-cyclic ethylene acetal]

A solution of 45 mg. of potassium hydroxide in 2.5 ml. of water at 0° C. is added dropwise to a solution of 40 mg. of (+)-3β-hydroxy-2α-(3 [S]-hydroxy-1-octenyl)-5-oxo-1β-cyclopentaneheptanoic acid methyl ester, 5-cyclic ethylene acetal in 1 ml. of methanol at 0° C. in a nitrogen atmosphere. The reaction mixture is allowed to warm to room temperature and stirred for 3 hours. Cold dilute aqueous potassium bicarbonate is added to the reaction mixture and the mixture extracted with hexane. Solid sodium dihydrogen phosphate is added to the aqueous layer and the latter is extracted with 1:1 ethyl acetate-benzene. The organic layer is dried over sodium sulfate and evaporated to dryness in vacuo affording (+)-prostaglandin $E_1$, 5-cyclic ethylene acetal [(+)-3β-hydroxy-2α-(3 [S]-hydroxy-1-octenyl)-5-oxo-1β-oxocyclopentaneheptanoic acid, 5-cyclic ethylene acetal] m.p. 82°–84° C.

When in the above procedure optically active 3β-hydroxy-2α-(3 [S]hydroxy-1-octenyl)-5-oxo-1β-cyclopentaneheptanoic acid methyl ester, 5-cyclic ethylene acetal of the natural series is employed in place of the racemic mixture there is obtained optically active prostaglandin $E_1$, 5-cyclic ethylene acetal of the natural series. m.p. 81°–83° C.

EXAMPLE 11

Prostaglandin $E_1$

A mixture of 37 mg. of (+)-prostaglandin $E_1$, 5-cyclic ethylene acetal and 3 ml. of 1:1 acetic acid-water is stirred at 25° C. for 3 hours. Saturated aqueous sodium hydrogen phosphate solution is added and the reaction mixture extracted with 1:1 ethyl acetate-benzene. The organic layer is washed with saturated aqueous sodium chloride, dried over sodium sulfate and evaporated to dryness in vacuo affording a crystalline residue which is recrystallized from ethyl acetate-benzene affording (+)-prostaglandin $E_1$, m.p. 111°–113° C.

When in the above procedure optically active prostaglandin $E_1$, cyclic ethylene acetal of the natural series is employed in place of the racemic mixture, there is obtained (−)-prostaglandin $E_1$, m.p. 112°–113° C., $[\alpha]_c^{THF}$ −58°.

What is claimed is:

1. 2α-(2-Carboxy-2-formylethyl)-3β-hydroxy-5-oxo-1β-cyclopentaneheptanoic acid, δ-lactone, 5-cyclic ethylene acetal, and stereoisomers and loweralkyl, benzyl, or xylyl esters thereof.

2. The compound of claim 1 in which the loweralkyl ester is the methyl ester.

3. The process for the preparation of the compound of claim 1 which comprises reacting the lower-alkyl or aralkyl ester of 2α-(2-Carboxyethyl)-3β-hydroxy-5-oxo-1β-cyclopentaneheptanoic acid, δ-lactone 5-cyclic ethylene acetal with a loweralkyl formate in the presence of an alkali metal hydride.

* * * * *